(12) United States Patent
Krupa

(10) Patent No.: US 8,440,871 B2
(45) Date of Patent: May 14, 2013

(54) TETRAMER PRODUCTION APPARATUS AND PROCESS RELATING THERETO

(75) Inventor: Steven Lee Krupa, Fox River Grove, IL (US)

(73) Assignee: UOP LLC, Des Plaines, IL (US)

( * ) Notice: Subject to any disclaimer, the term of this patent is extended or adjusted under 35 U.S.C. 154(b) by 156 days.

(21) Appl. No.: 13/007,131

(22) Filed: Jan. 14, 2011

(65) Prior Publication Data

US 2011/0245555 A1 Oct. 6, 2011

Related U.S. Application Data

(60) Provisional application No. 61/319,236, filed on Mar. 30, 2010.

(51) Int. Cl.
*C07C 5/00* (2006.01)

(52) U.S. Cl.
USPC .......................................................... 585/264

(58) Field of Classification Search .................... 585/264
See application file for complete search history.

(56) References Cited

U.S. PATENT DOCUMENTS

| | | | |
|---|---|---|---|
| 2,120,702 A | 6/1938 | Ipatieff et al. | |
| 2,519,343 A * | 8/1950 | Berg | 95/93 |
| 2,979,546 A * | 4/1961 | Grandio, Jr. et al. | 585/264 |
| 3,590,093 A * | 6/1971 | Crain et al. | 585/314 |
| 4,404,415 A | 9/1983 | Gaillard | |
| 4,513,156 A * | 4/1985 | Tabak | 585/329 |
| 4,835,331 A | 5/1989 | Hammershaimb et al. | |
| 5,245,107 A | 9/1993 | Yon et al. | |
| 5,271,835 A | 12/1993 | Gorawara et al. | |
| 5,371,301 A | 12/1994 | Marker et al. | |
| 5,689,014 A | 11/1997 | Frey et al. | |
| 5,705,712 A | 1/1998 | Frey et al. | |
| 5,908,964 A * | 6/1999 | Koskinen et al. | 568/697 |
| 6,107,526 A | 8/2000 | Frey et al. | |
| 6,111,159 A | 8/2000 | Huff et al. | |
| 6,124,517 A | 9/2000 | Kaminsky et al. | |
| 6,365,783 B1 | 4/2002 | Yokomori et al. | |
| 6,403,853 B1 | 6/2002 | Abrevaya et al. | |
| 6,580,009 B2 * | 6/2003 | Schwab et al. | 585/324 |
| 6,887,370 B2 * | 5/2005 | De Wet et al. | 585/862 |
| 7,102,049 B2 * | 9/2006 | Ding et al. | 585/639 |

(Continued)

FOREIGN PATENT DOCUMENTS

| | | |
|---|---|---|
| CN | 1379006 A | 11/2002 |
| JP | 6336590 A | 12/1994 |
| RU | 2263655 C1 | 11/2005 |
| WO | 03-033438 A1 | 4/2003 |

OTHER PUBLICATIONS

PCT-International Search Report, Date: Oct. 24, 2011, Intl. Appl. No. PCT/US2011/028931.

(Continued)

*Primary Examiner* — Jill Warden
*Assistant Examiner* — Huy-Tram Nguyen
(74) *Attorney, Agent, or Firm* — Maryann Maas

(57) ABSTRACT

One exemplary embodiment can be a tetramer production apparatus. The apparatus can include a fractionation zone and an oxygenate removal zone. The fractionation zone can produce a distillation product including one or more C6 hydrocarbons for producing one or more C12 compounds. The oxygenate removal zone may remove one or more oxygenate compounds from the distillation product passed through the oxygenate removal zone.

9 Claims, 1 Drawing Sheet

U.S. PATENT DOCUMENTS

| | | | |
|---|---|---|---|
| 7,186,328 | B1 | 3/2007 | Schultz et al. |
| 7,452,459 | B2 | 11/2008 | Schultz et al. |
| 7,737,312 | B2 | 6/2010 | Greager et al. |
| 2005/0209469 | A1* | 9/2005 | Shutt et al. ............ 549/523 |
| 2006/0084831 | A1 | 4/2006 | Zhang |
| 2006/0199987 | A1 | 9/2006 | Kuechler et al. |
| 2007/0038007 | A1* | 2/2007 | Greager et al. ............ 585/24 |
| 2010/0018899 | A1 | 1/2010 | Krupa et al. |

OTHER PUBLICATIONS

U.S. Appl. No. 12/509,182 filed Jul. 24, 2009, by Towler et al., entitled, "Process or System for Desorbing an Adsorbent Bed".

Asinger, "The Manufacture of the Higher Olefins by the Di-, Tri-, and Tetramerization of Normally Gaseous Olefins", Mono-Olefins, Chemistry and Technology, 1968, pp. 186-189.

Ginosar et al., "1-Hexene Reaction on a Pt/GAMMA-Al2O3 Catalyst: Some Insights into Coke Formation Chemistry", AIChE 1991 Annual Meeting, 1991, No. 91c, p. 14 pages.

Higashimura et al., "Cationic Oligomerization of 1-Hexene Catalyzed by EtAlCl2-Chloroacetic Acid Complexes", Journal of Applied Polymer Science, Jul. 1982, vol. 27, No. 7, pp. 2593-2603.

Jones, "Cumene and Tetramer Production", Petroleum Refiner, Dec. 1954, vol. 33, No. 12, pp. 186-187.

Krupa et al., "OXYPRO Process", Handbook of Petroleum Refining Processes, 2004, vol. 3rd ed., pp. 13.19-13.22.

* cited by examiner

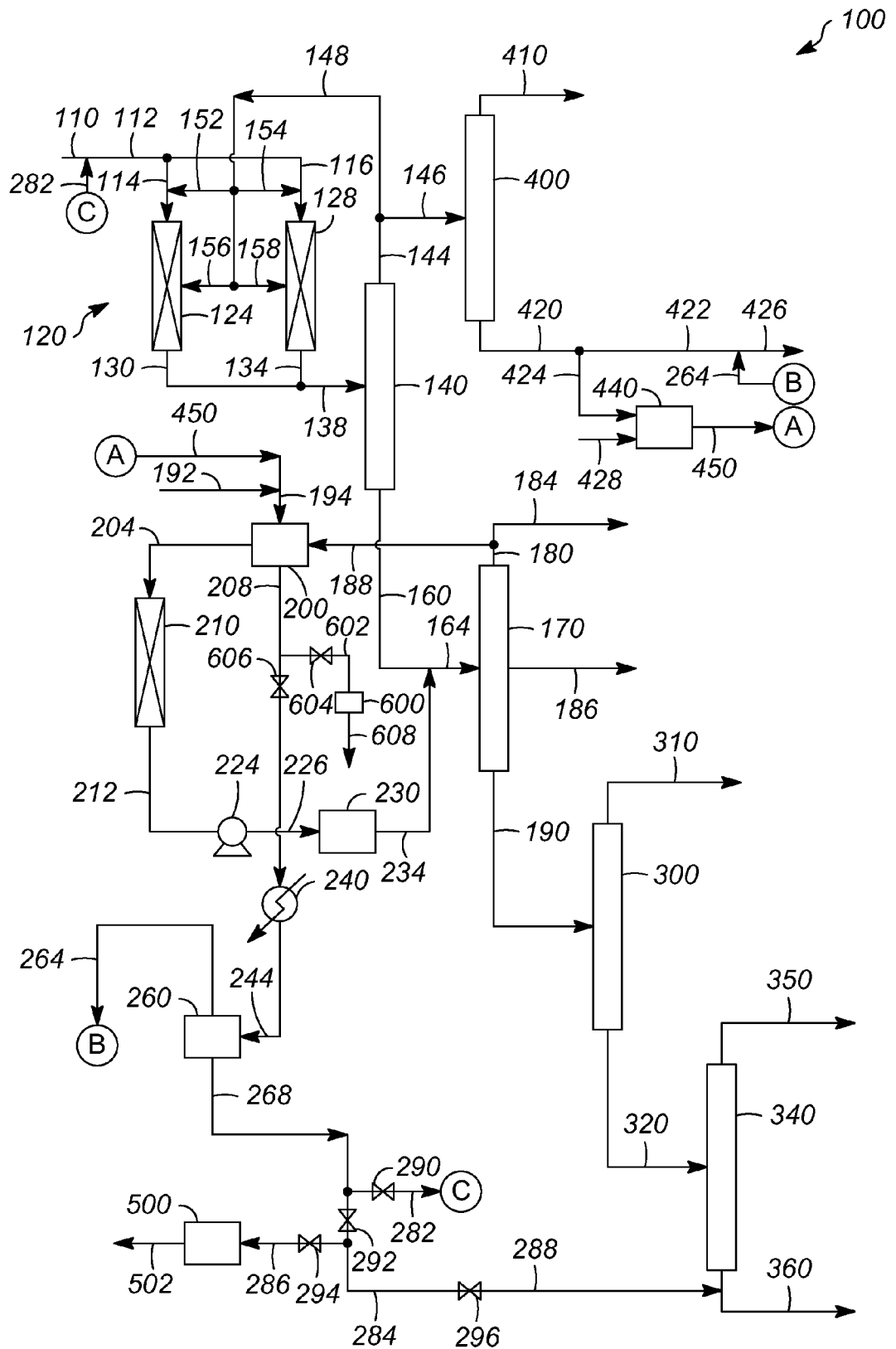

TETRAMER PRODUCTION APPARATUS AND PROCESS RELATING THERETO

CROSS-REFERENCE TO RELATED APPLICATIONS

This application claims the benefit of U.S. Provisional Application No. 61/319,236 filed Mar. 30, 2010, which is hereby incorporated by reference in its entirety.

FIELD OF THE INVENTION

This invention generally relates to a tetramer production apparatus and a relating process thereof.

DESCRIPTION OF THE RELATED ART

Catalytic processes for C9 and C12 tetramer production can utilize propene as a feedstock. In some instances, significant increases in the market price for C12 tetramer have occurred, and thus, a corresponding rise in C12 tetramer production is desired. Furthermore, such catalytic tetramer processes can produce significant amounts of C6-C7 alkene (or may referred hereinafter as "olefin") by-products that may be sold for non-petrochemical uses.

In such units, generally, a fractionation section follows a reaction section including a plurality of primary reactors. A column in the reaction section may produce a product having $C6^+$ hydrocarbons. Typically, the C6-C9 hydrocarbons may be recycled back to the reaction section to obtain more C12 alkenes based on the reaction of C6 alkenes and C9 alkenes with a feed of propene. However, this recycle can increase the hydraulic requirements of a first column in the fractionation section where C1-C4 hydrocarbons are separated from $C5^+$ hydrocarbons. Often these units may have a large recycle rate of C1-C4 hydrocarbons with a recycle/fresh-feed weight ratio of about 0.6:1-about 4.0:1. As a consequence, increased cost may be incurred to enlarge the first column to handle this additional hydraulic load. Moreover, such a recycle may also reduce catalyst life in the reaction section, and thus, may require additional catalyst and/or spare reactor vessels to minimize shutdowns, which can add to capital costs. Therefore, it would be desirable to react the fractionation cut rich in one or more C6-C8 compounds without recycling to the primary reactors to minimize the hydraulic impact upstream, obtain higher value products for the hydrocarbons present in that stream, minimize undesired byproducts, and increase catalyst life in the primary reactors.

However, light oxygenates can be present in this fractionation cut rich in one or more C6-C8 compounds. These oxygenates can include propanone, otherwise may be referred to as acetone; 2-butanone, otherwise may be referred to as methyl ethyl ketone; 2-propan-2-yloxypropane, otherwise may be referred to as diisopropyl ether or DIPE; and propan-2-ol, otherwise known as isopropyl alcohol. The presence of oxygenate can cause several problems, namely, affecting downstream production of units utilizing C12 tetramers as a feedstock, accumulating recycled heavier alcohols and ketones, producing carboxylic acid in the reactor effluent potentially resulting in the corrosion of equipment and/or costly preventative measures, and deactivating catalyst. As a consequence, it would be highly desirable to remove these oxygenates to prevent adverse effects.

SUMMARY OF THE INVENTION

One exemplary embodiment can be a tetramer production apparatus. The apparatus can include a fractionation zone and an oxygenate removal zone. The fractionation zone can produce a distillation product including one or more C6 hydrocarbons for producing one or more C12 compounds. The oxygenate removal zone may remove one or more oxygenate compounds from the distillation product passed through the oxygenate removal zone.

Another exemplary tetramer production apparatus may include a reaction zone, first, second, third, and fourth fractionation zones, and an oxygenate removal zone. The reaction zone can oligomerize propene to produce one or more $C6^+$ hydrocarbon products. Typically, the first fractionation zone produces an overhead stream including one or more $C4^-$ hydrocarbons and a bottom stream including one or more $C5^+$ hydrocarbons. The second fractionation zone can produce an overhead stream having one or more $C8^-$ hydrocarbons and a bottom stream having one or more $C9^+$ hydrocarbons. The third fractionation zone can produce an overhead stream including one or more $C11^-$ hydrocarbons and a bottom stream including one or more $C12^+$ hydrocarbons. Generally, the fourth fractionation zone produces an overhead stream having one or more $C14^-$ hydrocarbons and a bottom stream having one or more $C15^+$ hydrocarbons. Usually, the oxygenate removal zone has an adsorbent for removing one or more oxygenate compounds from a distillation product obtained from at least a portion of the overhead stream of the second fractionation zone and is passed through the oxygenate removal zone.

A further exemplary embodiment may be a process for producing one or more tetramers. The process can include passing a distillation product through an oxygenate removal zone to remove one or more oxygenates that may interfere with product production.

The embodiments provided herein can remove one or more oxygenates from the overhead of a column containing one or more $C6^+$ hydrocarbons. As such, removing such oxygenates can prevent several adverse effects. These adverse effects may include:

producing heavier oxygenates boiling in a C12 tetramer range that can fractionate into a C12 tetramer product;

poisoning of downstream petrochemical catalytic units utilizing the C12 tetramer feedstock;

accumulating heavier alcohol/ketones in the C6-C8 boiling range which can collect in a recycle to a reactor and interfere with C12 tetramer selectivity;

increasing production of carboxylic acids in the reactor effluent creating corrosion problems and expensive preventative measures, such as more costly and corrosion-resistant metals used in equipment such as piping and vessels, and reduced catalyst life and feed conversion; and deactivating catalyst by the production of propanone and 2-butanone.

As a consequence, the embodiments disclosed herein can eliminate these shortcomings by removing problematic oxygenate species. Often, a C12 tetramer product can be used as a feedstock to make a detergent, a polymer, or a petrochemical. Small amounts of oxygenates may interfere with such processes.

DEFINITIONS

As used herein, the term "stream" can be a stream including various hydrocarbon molecules, such as straight-chain, branched, or cyclic alkanes, alkenes, alkadienes, and alkynes, and optionally other substances, such as gases, e.g., hydrogen, or impurities, such as heavy metals, and sulfur and nitrogen compounds. The stream can also include aromatic and non-aromatic hydrocarbons. Moreover, the hydrocarbon molecules may be abbreviated C1, C2, C3 ... Cn where "n" represents the number of carbon atoms in the one or more hydrocarbon molecules or the abbreviation may be used as an adjective for, e.g., compounds. Furthermore, a superscript "+" or "−" may be used with an abbreviated one or more hydrocarbons notation, e.g., $C3^+$ or $C3^-$, which is inclusive of the abbreviated one or more hydrocarbons. As an example, the abbreviation "$C3^+$" means one or more hydrocarbon molecules of three carbon atoms and/or more. Moreover, a stream may include a feed, a product, an effluent, or a regenerant.

As used herein, the term "zone" can refer to an area including one or more equipment items and/or one or more sub-zones. Equipment items can include one or more reactors or reactor vessels, heaters, exchangers, pipes, pumps, compressors, and controllers. Additionally, an equipment item, such as a reactor, dryer, or vessel, can further include one or more zones or sub-zones.

As used herein, the term "rich" can mean an amount of generally at least about 50%, and preferably about 70%, by mole, of a compound or class of compounds in a stream.

As used herein, the term "substantially" can mean an amount of generally at least about 80%, preferably about 90%, and optimally about 99%, by mole, of a compound or class of compounds in a stream.

As used herein, the term "tetramer" can refer to a linear or branch alkene produced by reacting alkene molecules, such as ethene or propene, to form longer chain alkenes having four alkene units. Particularly, in one exemplary embodiment, propene can be reacted to form longer chain alkenes having C12 carbon atoms, although other tetramer species can be included in this definition, such as a C8 tetramer made from ethenes.

As used herein, the term "oligomer" can refer to reacting a monomer molecule, such as alkene, to form longer chain alkenes having 2, 3, or more units and can encompass a tetramer. As an example, propene can be reacted to form oligomers having 6, 9, or 12 carbon atoms.

As used herein, the term "paraffin" and "alkane" may be used interchangeably.

As used herein, the term "olefin" and "alkene" may be used interchangeably.

BRIEF DESCRIPTION OF THE DRAWING

FIG. 1 is a schematic depiction of an exemplary C12 tetramer production apparatus.

DETAILED DESCRIPTION

Referring to FIG. 1, an exemplary tetramer production apparatus 100 can include a reaction zone 120, a first fractionation zone 140, a second fractionation zone 170, an oxygenate removal zone 200, a dimerization reaction zone 210, a third fractionation zone 300, a fourth fractionation zone 340, and a fifth fractionation zone 400. In the FIGURE, any suitable shape may be used to indicate a zone, such as a square, a rectangle, or a crossed-rectangle. Moreover, the terms feed, stream, effluent, product, and regenerant may be used in the text when referring to the lines in the drawing.

The reaction zone 120 can include a first reactor 124 and a second reactor 128, and may receive a feed 110 that may be combined with a stream 282, as hereinafter described. Afterwards, this combined stream 112 can be split into streams 114 and 116, and routed to, respectively, the first reactor 124 and the second reactor 128. The tetramer production apparatus 100 can produce any suitable tetramers, such as C8, C12, and C16 tetramers or variants thereof by oligomerizing alkene monomers. Particularly, the tetramer production apparatus 100 can receive a feed of any suitable olefin, such as ethene, propene, butene, or mixture thereof, to produce a tetramer having a carbon number from C8-C16.

In one exemplary embodiment, the feed 110 can be substantially propene and yield oligomers of propene, such as a C6 alkene, a C9 alkene, and/or a C12 alkene, which may be linear or branched. Each reactor 124 and 128 can contain an acid catalyst, such as a solid phosphoric acid catalyst. In some preferred embodiments, an oxygenate, such as water, may be added to the feed 110. Moreover, the reactors 124 and 128 can operate, independently, at a temperature of about 50-about 350° C. and a pressure of about 1-about 7,000 kPa. Exemplary reactors and reactor conditions are disclosed in, e.g., U.S. Pat. No. 6,111,159 and U.S. Pat. No. 2,120,702. What is more, each reactor 124 and 128 may receive respective recycle streams 152 and 154 and respective quench streams 156 and 158, which will be described in further detail hereinafter. Each reactor 124 and 128 can produce, respectively, a first reactor effluent 130 and a second reactor effluent 134 that can be combined as a stream 138. This combined effluent stream 138 can be a feed to the first fractionation zone 140. Typically, the combined effluent stream 138 can include a variety of hydrocarbons, such as one or more $C1^+$ hydrocarbons.

The first fractionation zone 140 can receive the feed 138 and produce an overhead stream 144 including one or more hydrocarbons being $C4^-$ or boiling in the $C4^-$ range, and a bottom stream 160 including one or more hydrocarbons being $C5^+$ or boiling in the $C5^+$ range. The first fractionation zone 140 can include any suitable number of distillation columns or other separation vessels to provide these respective streams 144 and 160. The overhead stream 144 can be split into a stream 146, processing of which will be described hereinafter, and a stream 148, which, in turn, can be split into respective recycle streams 152 and 154 and respective quench streams 156 and 158. Generally, the stream 148 includes one or more $C4^-$ hydrocarbons and provided as quench streams 156 and 158 that can act to control the temperatures in each respective reactor 124 and 128. Moreover, the composition of the stream 148 can contain unreacted propene that can be recycled in the reaction zone 120, as recycle streams 152 and 154.

With respect to the bottom stream 160, the bottom stream 160 can be combined with an effluent stream 234, described hereinafter, and the combined streams 160 and 234 provided as a feed 164 to the second fractionation zone 170. The second fractionation zone 170 can produce an overhead stream or a distillation product 180 being rich in one or more hydrocarbons being $C8^-$ or boiling in the $C8^-$ range and a bottom stream 190 being rich in one or more hydrocarbons being $C9^+$ or boiling in the $C9^+$ range. Preferably, the overhead stream or distillation product 180 can include one or more C6 hydrocarbons. Moreover, the overhead stream 180 can be split to form a product stream 184 and a feed stream 188 to the oxygenate removal zone 200, as hereinafter described. In one exemplary embodiment, the overhead stream 180 can be rich in C5-C8 hydrocarbons and include about 40-about 50, by weight, hexenes based on the weight of the overhead stream 180. The second fractionation zone 170 can include any suitable number of distillation columns or other suitable separation devices. In one alternative embodiment, a side-stream 186 can be withdrawn from the second fractionation zone 170 to remove predominately one or more C8 hydrocarbons, which may also concentrate the amount of one or more C5-C7 hydrocarbons, preferably C6 alkenes, in the overhead stream 180. In such an instance, it may be desirable to have a product stream 184 of substantially one or more C5-C7 hydrocarbons to be used for other applications, such as non-petrochemical uses. In one exemplary embodiment, the feed stream 160 to the fractionation zone 170 can contain about 5.2%, by weight, of one or more C5-C7 alkenes and provide an overhead stream 180 that can contain almost about 100%, by weight, one or more C5-C7 alkenes based on the weight of the overhead stream 180. As such, the overhead stream 180 can contain about 8%, by weight, C5, about 70%, by weight, C6, and about 22%, by weight, C7 alkenes based on the weight of the overhead stream 180 and serve as a basis for a feed stream 204, as described hereinafter.

The bottom stream 190 can serve as a feed 190 adapted to be received by the third fractionation zone 300. The third fractionation zone 300 can provide an overhead stream 310 including one or more hydrocarbons being C11$^-$ or boiling in the C11$^-$ range, typically including one or more C9$^-$ alkenes. In addition, the bottom stream 320 can include one or more hydrocarbons being C12$^+$ or boiling in the C12$^+$ range. Thus, the third fractionation zone 300 can include any suitable number of distillation columns or other devices and operated under any suitable conditions to provide the requisite separation.

The bottom stream 320 can act as a feed 320 adapted to be received by the fourth fractionation zone 340. Generally, the fourth fractionation zone 340 includes any suitable number of distillation columns or other devices and operated under any suitable conditions to provide the requisite separation for producing an overhead stream 350 and a bottom stream 360. Often, the overhead stream 350 can include one or more hydrocarbons being C14$^-$ or boiling in the C14$^-$ range, which can contain the desired C12 product, such as a C12 tetramer product. The bottom stream 360 can include one or more hydrocarbons being C15$^+$ or boiling in the C15$^+$ range, and may be utilized as, for example, fuel oil. In addition, the bottom stream 360 can receive a stream 288, as described further hereinafter.

All the fractionation zones described herein provide a split of hydrocarbon molecules, e.g., C4$^-$ and C5$^+$, or hydrocarbons boiling in the C4$^-$ and C5$^+$ ranges, but it should be understood that other hydrocarbon molecules outside these ranges, such as, e.g., relatively small amounts of pentane for C4$^-$, may be included. Often such overhead streams or bottom streams are rich in the indicated hydrocarbons, e.g., the overhead stream 310 may be rich in the one or more hydrocarbons boiling in the C11$^-$ range.

The feed stream 188 split from the overhead stream 180 of the second fractionation zone 170 can be provided to the oxygenate removal zone 200 for removing one or more oxygenates. The oxygenates may include one or more of acetone, methyl ethyl ketone, diisopropyl ether, and isopropyl alcohol, and ketones and alcohols boiling in the C5-C8 hydrocarbon range. Any suitable oxygenate removal zone 200 may be utilized. As such, the oxygenate removal zone 200 may include an adsorbent, a wash system, or a liquid-liquid extraction unit. If a wash system is used, such as a sodium bisulfite wash system, light alcohols and ketones may be removed from a stream 188 containing no more than about 5%, by weight, heavy oxygenates based on the weight of the stream 188. Typically, the stream 188 can include no more than about 5%, by weight, preferably no more than about 2.5%, by weight, and optimally no more than about 1%, by weight, of oxygenates. Generally, the oxygenate levels at the outlet of the oxygenate removal zone 200 can generally be no more than about 100 ppm, by weight, preferably no more than about 10 ppm, by weight, and optimally no more than about 1 ppm, by weight, with respect to the weight of the effluent stream 204. Usually, the oxygen removal zone 200 should be sufficient to meet the product specifications of any C12 alkene product to avoid accumulation of oxygenates in the feed to the reaction zone 210 due to recycling, and to minimize carboxylic acid production in the reaction zone 210. Moreover, minimizing the recycling of oxygenates can reduce the negative impact on catalyst activity or performance in the reaction zone 210.

In this exemplary embodiment as depicted, the oxygenate removal zone 200 can be an adsorptive removal zone 200 and include one or more, preferably two or more, adsorbent beds. Any suitable molecular sieve can be utilized as the adsorbent, which can be a zeolite, a silica gel, or an activated alumina. Generally, the molecular sieve can include a zeolite X, Y, L, or a combination thereof. In addition, the adsorption conditions can be about 20-about 80° C. and a pressure of about 100-about 3,500 kPa. Generally, after adsorption, the adsorbent bed is desorbed. The regeneration conditions can include a temperature of about 200-about 320° C. and a pressure of about 100-about 3,500 kPa. Generally, a regenerant or desorbent stream 194 is in a gas phase, as discussed hereinafter. An exemplary removal zone 200 is disclosed in, e.g., U.S. Pat. No. 5,271,835 or U.S. Pat. No. 6,107,526. An effluent 204 from the oxygenate removal zone 200 can be provided to the dimerization reaction zone 210.

Desirably, the dimerization reaction zone 210 can react one or more C6 alkenes to form one or more C12 and higher alkenes. Generally, the concentration of C6 alkene is dependent on the type of catalyst utilized. Particularly, some catalysts may be more selective for the desired C6 alkene reaction in the presence of other potentially reactive olefins, such as C7 and C8 alkenes. A catalyst that has activity for increased C7 and C8 alkene reactivity may also make C13 and C14 alkene by-products, which can significantly reduce the desired C12 alkene production. Usually, increasing the C6 alkene purity in the overhead stream 180 boosts the utility expense or extra capital costs for additional trays to provide the requisite separation. Withdrawing C7 and C8 alkenes with the C9 alkenes may be undesirable depending on, e.g., the value of the C9 alkenes. An additional side-stream of C7 and C8 alkenes may be withdrawn from the column of the second fractionation zone 170 when desiring a higher C6 alkene content overhead for a feed to the hexene dimerization reaction zone 210. The composition of the stream 180 may be adjusted upon the catalyst in the reaction zone 210.

The dimerization reaction zone 210 can include any suitable catalyst that can be active for olefin oligomerization, such as various one or more acidic catalysts, including zeolite catalysts. Typically, the catalyst pore size may be chosen to control or optimize specific product properties, such as the degree of branching or carbon number of oligomers. Generally, zeolite acidity may be optimized by, e.g., varying the silica to alumina ratio. Exemplary catalysts are disclosed in, e.g., US 2006/0199987 A1. The reaction can occur at a temperature of about 70-about 300° C., and a pressure of about 1,200-about 7,000 kPa. Desirably, the reaction provides one or more C12 oligomers.

Although not shown, a portion of the effluent from the reactor outlet can be recycled to control the temperature of the reactor inlet of the reaction zone 210. Generally, a cooler may be used to remove the exothermic heat of reaction and provide a cooled recycle stream to the reactor inlet.

The effluent 212 from the dimerization reaction zone 210 can be provided to a fluid transfer device 224, such as a pump, and be provided to a treatment zone 230. Generally, the treatment zone 230 includes a treater that can use an adsorbent such as activated charcoal, hydrotalcite, ion exchange resin, a zeolite, a silica-alumina and/or a silica gel. Contacting of the discharge stream 226 can be conducted at a temperature of about 25-about 160° C., and a pressure to maintain components in a liquid phase, such as a pressure of about 100-about 1,800 kPa, and a liquid hourly space velocity (may be abbreviated LHSV) of about 5-about 50 hr$^{-1}$. Generally, the treatment zone 230 can remove any acid, such as trace amounts of acid originating from a catalyst and trace amounts of acid from oxygenate conversion in the reaction zone 210 effluent. One or more exemplary treatment zones are disclosed in, e.g., U.S. Pat. No. 5,689,014. An effluent stream 234 from the treatment zone 230 can be combined with the bottom stream 160 of the first fractionation zone 140, as discussed above.

The C6-C24 alkenes, primarily C9-C12 alkenes, formed by the reaction in the effluent stream 234 may be separated in the secondary fractionation zone 170 into the bottom stream 190, and then onward to the third fractionation zone 300 and the fourth fractionation zone 340 where C9 and C12 alkene products may be recovered. Generally, the excess hydraulic capacity at the top of the column in the second fractionation zone 170 may be exploited by recycling the reaction effluent back to the column inlet and allow the reaction to be operated at a lower per pass conversion of C6-C8 alkenes. This may limit the concentration of C12 and C13 alkene reaction products in the reaction effluent, which may reduce the extent that these species further react to make undesired heavier oligomers, such as one or more C18-C20 alkenes. The recycle flow may be set to optimize the C12 and C13 selectivity within the constraint of the hydraulic limits at the top of the column in the fractionation zone 170. The net overhead product can exit on a level control and consist primarily of unconverted C5-C8 alkenes. If operated at a low-per-pass conversion, the amount of one or more C12 alkenes further reacted to produce undesired heavier oligomers can be minimized. If the hydraulic constraints at the top of the column in the fractionation zone 170 do not allow the full return of the reaction zone 210 effluent recycle back to the column inlet, a flash drum may be added to provide a smaller flow of C12 alkene enriched liquid that may be recycled to the column inlet most likely without causing hydraulic problems at the top of the column.

Referring to the first fractionation zone 140 and a desorbent stream for the oxygenate removal zone 200, the stream 146 that may be split from the overhead stream 144 can be provided to the fifth fractionation zone 400. The fifth fractionation zone 400 can provide an overhead stream 410 including one or more hydrocarbons being C2$^-$ or boiling in the C2$^-$ range and a bottom stream 420 including one or more hydrocarbons being C3$^+$ or boiling in the C3$^+$ range. The bottom stream 420 can include at least about 85%, by weight, propane, no more than about 15%, by weight, propene, and no more than about 0.5%, by weight, isobutane. A portion of the bottom stream 420 can be withdrawn as a stream 424 and sent to the complete saturation zone 440. The remaining portion, namely a stream 422, can be combined with a vent stream 264 from "B" and leave the apparatus 100 as a stream 426. The stream 426 can be used in any suitable application, such as fuel gas, liquefied petroleum gas bottling, or aerosols.

The stream 424 entering the complete saturation zone 440 can be partially or completely saturated to provide a regenerant comprising one or more saturated C3 hydrocarbons or a saturated or regenerant stream 450. Generally, the complete saturation zone 440 receives a hydrogen stream 428 to complete the saturation process. Usually, the conditions in the complete saturation zone 440 are sufficient, e.g., temperature and pressure, to saturate the alkenes and substantially convert them to alkanes. One exemplary catalyst can be a noble metal, such as palladium, hydrogenation catalyst operated at a temperature of about 20-about 80° C. and a pressure of about 2,000-about 3,500 kPa. An exemplary complete saturation zone 440 is disclosed in, e.g., U.S. Pat. No. 6,107,526. The complete saturation zone 440 can provide a regenerant stream 450 including one or more saturated C3$^+$ hydrocarbons. As such, the regenerant stream 450 can include less than about 0.1%, by weight, alkenes, preferably less than about 0.01%, by weight, alkenes.

The regenerant stream 450 from "A" can be used to regenerate the oxygenation removal zone 200. Particularly, the regenerant stream 450 can be combined with a stream 192 including one or more C4 hydrocarbons, including one or more C4 alkanes, to provide a combined feed 194 to the oxygenate removal zone 200. The regeneration conditions can include a temperature of about 200-about 300° C. and a pressure of about 100-about 3,500 kPa. Generally, the regenerant or desorbent stream 194 is in a gas phase. Typically, a vaporizer and/or electric superheater may be provided to obtain the requisite regeneration temperature. Alternatively, a small heat exchanger can be used to provide the proper heating for the regenerant stream 194 by using the bottom streams from one of the fractionation zones, e.g., the first fractionation zone 140 or the third fractionation zone 300.

The regenerant stream 194 is typically a stream free of olefins and other unsaturates. Alternatively, a suitable external regenerant, such as fuel gas or nitrogen, can be used. A benefit of using propane present in the apparatus 100 is minimizing the amount of make-up propane.

After desorbing an adsorbent bed, an effluent stream 208 can exit the oxygenate removal zone 200 and pass through a valve 606 with a valve 604 closed. Subsequently, this effluent stream 208 can pass through an exchanger 240, such as a cooling water condenser, to provide a cooled stream 244 to enter at least one flash drum 260. The flash drum 260 can be at any suitable pressure where the isobutane can escape as a gas and the heavy oxygenates may condense out as liquids. Typically, the flash drum 260 may be at a temperature of about 20-about 70° C. and a pressure of about 130-about 210 kPa. If the regenerant primarily includes C3 hydrocarbons, a slightly higher pressure may be used than if isobutane is primarily used as a regenerant. A vent stream 264 at "B" from the flash drum 260 after cooling to a liquid phase and being pumped can be combined with the stream 422, which may be split from the bottom stream 420 of the fifth fractionation zone 400. Alternatively, if the vent stream 264 is maintained in a gas phase, it can be routed to fuel gas or offgas. Usually, the vent stream 264 can include, independently, one or more C4$^-$ hydrocarbons. The bottom stream 268, which may include one or more hydrocarbons boiling or fractionating in a C6-C8 hydrocarbon range, can then be provided to at least one of several dispositions. Typically, the one or more hydrocarbons can substantially be one or more oxygenates, and include hydrocarbons having less than 6 carbon atoms, but boil or fractionate in the C6-C8 hydrocarbon range, such as methyl ethyl ketone.

As an example, at least a portion or all of a stream 282 can be recycled at "C" and combined with the feed 110 to the reaction zone 120 by opening a valve 290 and/or a valve 292. At least a portion of the stream 268 can be split into streams 284 and 286 by opening the valve 292 and valves 294 and/or 296. By opening the valve 294, a stream 286 can be sent to an oxygenate decomposition reaction zone 500.

Typically, the oxygenate decomposition reaction zone 500 can convert the oxygenates into another compound, such as water, that can be easily separated from the hydrocarbon. Alternatively, any ketones can be hydrogenated to alcohols. As such, the oxygenate decomposition reaction zone 500 can utilize any suitable full or partial hydrogenation reaction to convert the oxygenates to desired compounds. Afterwards, an effluent 502 can exit the oxygenate decomposition reaction zone 500 and exit the apparatus 100 for utilization in any suitable application. Opening the valve 296 can divert at least a portion of the stream 284 as a stream 288, which in turn can be combined with the bottom stream 360 of the fourth fractionation zone 340 and be used as, for example, fuel oil. Thus, the combined stream 268 can be sent to at least one of these three destinations, namely the oxygenate decomposition reaction zone 500, the feed 110, and the bottom stream 360, by manipulating the valves 290, 292, 294, and 296.

The desorbent effluent stream 208 may also be processed through an alcohol decomposition zone 600. In this exemplary embodiment, the valve 606 may be closed or partially opened to permit at least some of the desorbent effluent stream 208 to pass through the valve 604 as a feed stream 602 to the alcohol decomposition zone 600. The alcohol decomposition zone 600 can include an alumina or any other suitable catalyst to dehydrate the alcohols to yield one or more C5-C8 boiling range ketone-rich products. The alumina bed for alcohol decomposition can be installed directly on the spent regenerant prior to the exchanger 240 to utilize the high regeneration temperature. As such, the at least one flash drum 260 may require a boot to drain off any resulting water. An effluent 608 from the zone 600 can be withdrawn and sent to any suitable product destination.

Other alternative embodiments are also contemplated. As an example, the oxygenate removal zone 200 can be placed downstream of the reaction zone 210. Particularly, for some catalysts, oxygenates can affect the selectivity of the catalyst. In particular, removing oxygenates from the feed stream 204 may significantly increase the C7-C8 alkene conversion and cause increased C13-C14 alkene by-products with less of the desired C12 alkenes. As a consequence, the oxygenate removal zone 200 can optionally be moved downstream.

The one or more C12 alkenes obtained by the embodiments disclosed herein can be used in the manufacture of polymers and petrochemicals. In addition, the C12 alkenes may be used as a petrochemical feedstock to make C13 plasticizers. Thus, the C12 alkenes can be used in the production of alkyl phenols as part of the process to make lubricant additives and as a feedstock for synthetic detergents. At least in some of these processes, low levels of oxygenates can affect subsequent reactions of the C12 alkenes to form the desired products. As a consequence, it is desirable to remove the oxygenates to avoid these undesirable side reactions.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing, all temperatures are set forth in degrees Celsius and, all parts and percentages are by weight, unless otherwise indicated.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A tetramer production apparatus comprising:
   A) a fractionation zone producing a distillation product comprising one or more C6 hydrocarbons for producing one or more C12 compounds; and
   B) an oxygenate removal zone comprising an adsorptive removal zone comprising an adsorbent for removing one or more oxygenate compounds from the distillation product passed through the oxygenate removal zone
   C) an oxygenate removal zone feed conduit in fluid communication with the fractionation zone and with the oxygenate removal zone and a regeneration conduit in fluid communication with the oxygenate removal zone and another fractionation zone.

2. The apparatus according to claim 1, further comprising a treatment zone downstream of the oxygenate removal zone.

3. The apparatus according to claim 2, further comprising a fluid transfer device upstream of the treatment zone.

4. The apparatus according to claim 2, wherein the treatment zone communicates an effluent to the fractionation zone.

5. The apparatus according to claim 1, further comprising a reaction zone for oligomerizing propene.

6. The apparatus according to claim 5, wherein the fractionation zone is a second fractionation zone and the apparatus further comprises a first fractionation zone, wherein the first fractionation zone is adapted to receive an effluent from the reaction zone and provides an overhead stream comprising one or more C4− hydrocarbons and a bottom stream comprising one or more C5+ hydrocarbons.

7. The apparatus according to claim 6, further comprising:
   a third fractionation zone adapted to receive a bottom stream from the second fractionation zone; and
   a fourth fractionation zone adapted to receive a bottom stream from the third fractionation zone.

8. The apparatus according to claim 7, further comprising:
   wherein the another fractionation zone is a fifth fractionation zone adapted to receive the overhead stream from the first fractionation zone and provide a stream comprising one or more $C3^+$ hydrocarbons to a complete saturation zone, which in turn provides a regenerant comprising one or more saturated $C3^+$ hydrocarbons.

9. The apparatus of claim 7
   wherein the reaction zone for oligomerizing propene produces one or more $C6^+$ hydrocarbon products;
   wherein the third fractionation zone comprises an overhead stream comprising one or more $C11^-$ hydrocarbons and a bottom stream comprising one or more $C12^+$ hydrocarbons;
   wherein the fourth fractionation zone comprises an overhead stream comprising one or more $C14^-$ hydrocarbons and a bottom stream comprising one or more $C15^+$ hydrocarbons;
   wherein the oxygenate removal zone comprises an adsorbent for the removing one or more oxygenate compounds from the distillation product; and
   wherein the oxygenate removal zone feed conduit is in fluid communication with the second fractionation zone and the regeneration conduit in fluid communication with the fifth fractionation zone.

* * * * *